United States Patent [19]

Herbstritt et al.

[11] Patent Number: 5,965,374
[45] Date of Patent: Oct. 12, 1999

[54] GLUCAN-SPECIFIC ASSAY

[75] Inventors: Christopher J. Herbstritt; Michael G. Pepe, both of Frederick, Md.

[73] Assignee: BioWhittaker Technologies, Inc., Wilmington, Del.

[21] Appl. No.: 08/951,462

[22] Filed: Oct. 16, 1997

[51] Int. Cl.$^6$ .................. G01N 33/53; G01N 33/567; C07K 16/00; C12P 21/08
[52] U.S. Cl. .................. 435/7.1; 435/7.2; 435/975; 530/388.2; 530/388.25; 530/388.7
[58] Field of Search ............... 435/7.1, 7.2, 975; 530/388.2, 388.25, 388.7

[56] References Cited

U.S. PATENT DOCUMENTS 4,510,241   4/1985   Mills .

FOREIGN PATENT DOCUMENTS

| 049161 | 4/1982 | European Pat. Off. . |
| 0 291 856 | 11/1988 | European Pat. Off. . |
| 0 491 047 | 6/1992 | European Pat. Off. . |
| 0 500 947 | 9/1992 | European Pat. Off. . |

OTHER PUBLICATIONS

Umans, et al., "Targeted Inactivation of the Mouse $\alpha_2$—Macroglobulin," J. of Biological Chem., vol. 270, No. 34, 19778–19785, 1995.

Iwaki, et al, "Molecular Cloning of Limulus $\alpha_2$—macroglobulin," Eur. J. Biochem, vol. 242, 822, 1996.

Dolmer, et al., "Localisation of the Major Reactive Lysine Residue Involved in the Self–Crosslinking of Proteinase–Activated Limulus $\alpha_2$—macroglobulin," FEBS Letters, vol. 393, 37–40, 1996.

Armstrong, et al., "The Limulus Blood Cell Secretes $\alpha_2$—Macroglobulin When Activated," Biol. Bull., vol. 178, 137–143, Apr. 1990.

Lysiak, et al., "$\alpha_2$—Macroglobulin Functions as a Cytokin Carrier to Induce Nictric Oxide Synthesis and Cause Nitric Oxide–dependent Cytotoxicity in the RAW 264.7 Macrophage Cell Line," J. of Biological Chem., vol. 270, No. 37, 21919–21927, Sep. 15, 1995.

Pierce Corporate Bulletin, "ImmunoPure® Plus Immbolized Protein G," 1–5, 1995.

ClonaCell™—HY Hybridoma Cloning Kit Technical Kit, Aug. 1996.

Overberg, et al., "Identification of Four Genes Coding For Isoforms of Murinoglobulin, The Monomeric Mouse Alpha 2–macroglobulin: Characterization of the Exons Coding For the Bait Region," Genomics, vol. 22, 530–539, Aug. 1994 (Abstract).

Webb, et al., "Murine Alpha–Macroglobulins Demonstrate Divergent Activities As Neutralizers of Transforming Growth Factor–Beta and as Inducers of Nitric Oxide Synthesis. A Possible Mechanism for the Endotoxin Insensitivity of the Alpha2–macroglobulin Gene Knock–out Mouse," J. Biol. Chem, vol. 271, No. 4, 24982–24988, Oct. 1996 (Abstract).

Koo, et al., "Interaction of Nerve Growth Factor With Murine Alpha–Macroglobulin," J. Neurosci. Res. vol. 22, No. 3, 247–261, Mar. 1989 (Abstract).

Zorin, et al., "The Detection of Streptococcal Cell–Wall Proteins that Form Complexes With Human Macroglobulins," Zh Mikrobiol Epidemiol Immunobiol, vol. 8, 9–11, 1990 (Abstract).

Borth, et al., "Binding of IL–1 Beta to Alpha–Macroglobulins and Release by Thioredoxin," J. Immunol, vol. 145, No. 11, 3747–3754, Dec. 1990 (Abstract).

Bonner, et al., "Alpha–Macroglobulin Secreted by Alveolar Macrophages Serves as a Binding Protein for a Macrophage–Derived Homologue of Platelet–Derived Growth Factor," Am. J. Respir. Cell Mol. Biol., vol. 1, No. 3, 171–179, 1989 (Abstract).

Lasson, "Acute Pancreatitis in Man. A Clinical and Biochemical Study of Pathophysiology and Treatment", Scand J. Gatroentreol Suppl., vol. 99, 1–57, 1984 (Abstract).

Armstrong et al., "$\alpha 2$—macroglobulin; A recently discovered defease system in arthropods," *Immunology of Insects and Other Arthropods* (Gupta, ed.), Chapter 10, pp. 291–210, 1991.

T.J. Novitsky "LAL: Discovery and Commercial Development," in LAL Update Newsletter, Jun. 1996, pp. 1–8.

Zang, et al., "Differential Blocking of Coagulation–Activating Pathways of Limulus Amebocyte Lysate" Journal of Chemical Microbiology, 1537–1541, 1994.

G. Zhang et al. "Sensitive quantiation of endotoxin by enzyme–linked immunosorbent assay with monoclonal antibody against Limulus peptide C" Journal of Clinical Microbiology, vol. 32, No. 2, 1994, pp. 416–422.

M. Pepe et al. "Isolation and characterization of endotoxin binding proteins from Limulus amebocyte lysate" Journal of Endotoxin Research, vol. 3, No. Suppl. 1, 1996, p. 51.

*Primary Examiner*—Anthony C. Caputa
*Assistant Examiner*—Mark Navarro
*Attorney, Agent, or Firm*—Banner & Witcoff, Ltd.

[57] ABSTRACT

The present invention is directed to monoclonal antibodies which specifically bind to a Limulus $\alpha_2$-macroglobulin. Preferred monoclonal antibodies inhibit the enzymatic activation of a Limulus amebocyte lysate to form a gel or to cleave a chromogenic substrate in the presence of an endotoxin but not in the presence of a glucan. The monoclonal antibodies can be used, inter alia, to purify a Limulus $\alpha_2$-macroglobulin, and the preferred antibodies can be used in a method for specifically detecting a glucan in a test sample using an amebocyte lysate.

8 Claims, 1 Drawing Sheet

Inhibition of LAL with anti Alpha 2 Mac Ab

A2M-3

| µg/ml | %I, 7A10 | %I, 2D5 |
|---|---|---|
| 0.000 | 0.000 | 0.000 |
| 1.560 | 18.400 | 8.220 |
| 3.125 | 64.000 | 7.400 |
| 6.250 | 100.000 | 12.300 |

GLUCAN-SPECIFIC ASSAY

TECHNICAL AREA OF THE INVENTION

The invention relates to the area of glucan detection. More particularly, the invention relates to the detection of glucan using a Limulus amebocyte lysate.

BACKGROUND OF THE INVENTION

Limulus amebocyte lysate undergoes clot (gel) formation along two enzymatic pathways. These enzymatic pathways comprise a series of serine proteases which are activated in the presence of either endotoxin or glucan. Limulus amebocyte lysate is widely used in assays, which take advantage of this activity, for detecting the presence of endotoxins, for example in water and in a variety of biological test samples.

Because the Limulus amebocyte lysate is much more sensitive to the presence of endotoxin than to glucan, however, the prior art has been unable to develop a successful glucan assay using Limulus amebocyte lysate (LAL). The presence of just a small amount of endotoxin in a test sample results in a false positive result when attempting to detect glucan using LAL. Thus, there remains a need in the art for a method which can be used for specifically detecting glucan in a test sample.

SUMMARY OF THE INVENTION

It is an object of the invention to provide an isolated and purified monoclonal antibody.

It is another object of the invention to provide a hybridoma cell which produces a monoclonal antibody which specifically binds to Limulus $\alpha_2$-macroglobulin.

It is yet another object of the invention to provide a solid substrate for use in purifying Limulus $\alpha_2$-macroglobulin.

It is still another object of the invention to provide a method of purifying Limulus $\alpha_2$-macroglobulin.

It is still another object of the invention to provide a method and reagent for specifically detecting a glucan in a test sample.

It is a further object of the invention to provide a kit for specifically detecting a glucan in a test sample.

These and other objects of the invention are provided by one or more of the embodiments described below.

One embodiment of the invention provides an isolated and purified monoclonal antibody which specifically binds to a Limulus $\alpha_2$-macroglobulin.

Another embodiment of the invention provides a hybridoma cell which produces a monoclonal antibody, which specifically binds to a Limulus $\alpha_2$-macroglobulin.

Yet another embodiment of the invention provides a solid substrate for use in purifying a Limulus $\alpha_2$-macroglobulin. The solid substrate comprises a monoclonal antibody which specifically binds to the Limulus $\alpha_2$-macroglobulin.

Still another embodiment of the invention provides a reagent for specifically detecting a glucan in a test sample. The reagent comprises an amebocyte lysate and a monoclonal antibody which binds to a Limulus $\alpha_2$-macroglobulin. Addition of the monoclonal antibody to the amebocyte lysate inhibits enzymatic activation of the amebocyte lysate in the presence of an endotoxin but not in the presence of a glucan.

Even another embodiment of the invention provides a method of specifically detecting a glucan in a test sample. An amebocyte lysate is contacted with a monoclonal antibody which specifically binds to a Limulus $\alpha_2$-macroglobulin. Addition of the monoclonal antibody to the amebocyte lysate inhibits enzymatic activation of the amebocyte lysate in the presence of an endotoxin. The amebocyte lysate is then contacted with the test sample. Enzymatic activation of the amebocyte lysate indicates the presence of a glucan in the test sample.

Yet another embodiment of the invention provides a method of purifying a Limulus $\alpha_2$-macroglobulin. A solid substrate comprising a monoclonal antibody which binds to the Limulus $\alpha_2$-macroglobulin is contacted with a Limulus amebocyte lysate under conditions wherein the monoclonal antibody reversibly binds to the $\alpha_2$-macroglobulin in the Limulus amebocyte lysate. Proteins which are not specifically bound to the monoclonal antibody are removed from the solid substrate. The $\alpha_2$-macroglobulin is then released from the monoclonal antibody. Upon its release from the monoclonal antibody, the $\alpha_2$-macroglobulin is substantially free from other proteins of the Limulus amebocyte lysate.

A further embodiment of the invention provides a kit for specifically detecting a glucan in a test sample. The kit comprises an amebocyte lysate and a monoclonal antibody which binds to a Limulus $\alpha_2$-macroglobulin. Addition of the monoclonal antibody to the amebocyte lysate inhibits enzymatic activation of the amebocyte lysate in the presence of an endotoxin but not in the presence of a glucan.

The present invention thus provides the art with monoclonal antibodies which specifically bind to a Limulus $\alpha_2$-macroglobulin. The monoclonal antibodies can be used, inter alia, to purify Limulus $\alpha_2$-macroglobulin and in a method for specifically detecting a glucan in a test sample using an amebocyte lysate.

BRIEF DESCRIPTION OF THE DRAWINGS

FIG. 1 demonstrates the inhibition of the response of a Limulus amebocyte lysate to endotoxin in the presence of the monoclonal antibody 7A10.

DETAILED DESCRIPTION OF THE PREFERRED EMBODIMENTS

Figure 1:
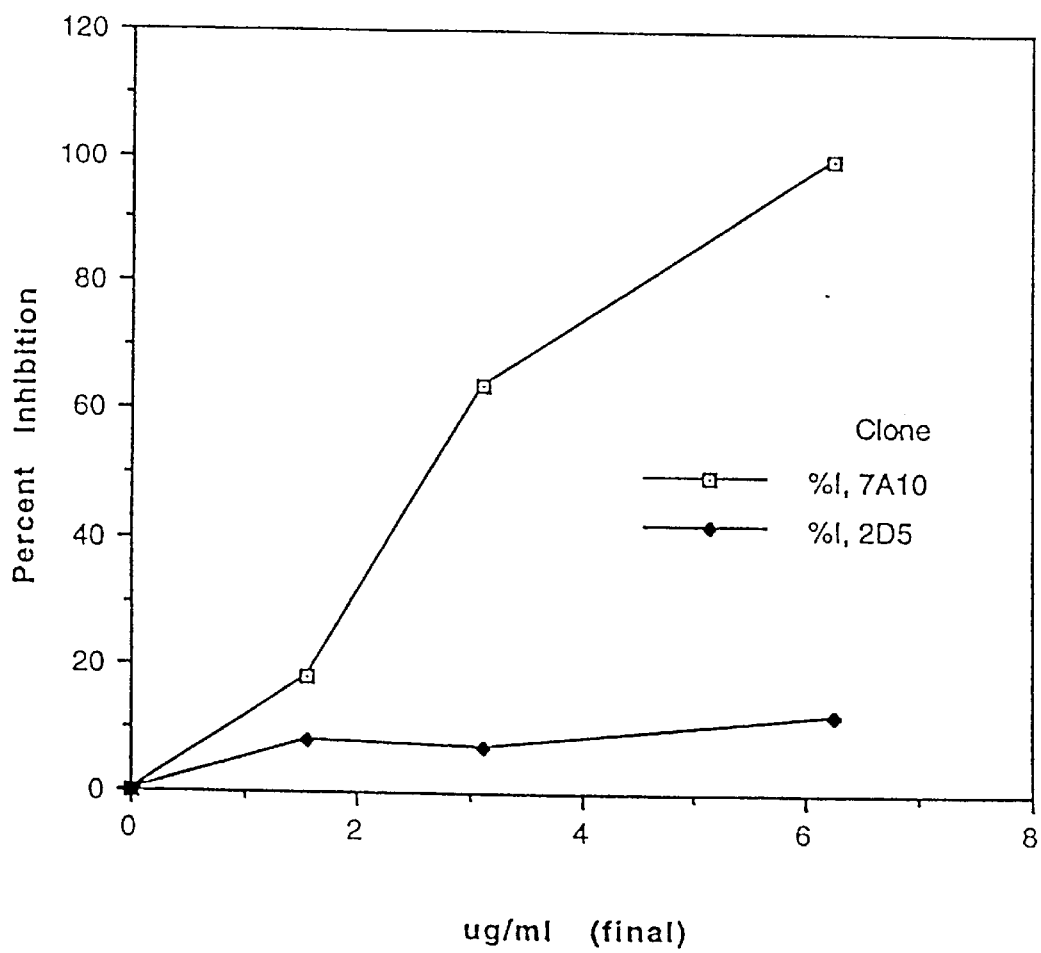
FIG. 1.

Monoclonal antibodies which specifically bind to Limulus $\alpha_2$-macroglobulin are herein disclosed. It is a discovery of the present invention that certain of the monoclonal antibodies which specifically bind to Limulus $\alpha_2$-macroglobulin can inhibit enzymatic activation of a Limulus amebocyte lysate in response to endotoxin but not to glucan. Limulus $\alpha_2$-macroglobulin-specific monoclonal antibodies also can be used to purify Limulus $\alpha_2$-macroglobulin and to generate a glucan-specific assay from the Limulus amebocyte lysate. Limulus $\alpha_2$-macroglobulin, a general protease inhibitor, is present in the amebocyte lysate of horseshoe crabs, *Limulus polyphemus*. An amino acid sequence of Limulus $\alpha_2$-macroglobulin is disclosed in Iwaki et al., *Eur. J. Biochem:* 242, 822 (1996), which is incorporated herein by reference. Previous studies have indicated, however, that purified $\alpha_2$-macroglobulin does not inhibit the serine proteases involved in lysate gel clot formation associated with the endotoxin reaction (Iwaki et al., 1996). Thus, it was surprising to find that a monoclonal antibody which specifically binds to Limulus $\alpha_2$-macroglobulin would have an inhibitory effect on the enzyme cascade in the Limulus amebocyte lysate in response to the presence of endotoxin.

In accordance with the present invention, purified Limulus $\alpha_2$-macroglobulin can be used as an immunogen to generate monoclonal antibodies, useful in practicing the various embodiments of the present invention, using standard hybridoma technology. The monoclonal antibodies can be generated using the ClonaCell™-HY hybridoma cloning kit (StemCell Technologies Inc.), according to the technical manual which accompanies the kit. The kit comprises a methylcellulose-based medium which contains growth factors, B-cell stimulators, and medium supplements which promote the growth of single cells.

Limulus $\alpha_2$-macroglobulin used as an immunogen in the process of generating a monoclonal antibody can be purified using standard biochemical techniques such as size exclusion chromatography, ammonium sulfate fractionation, ion exchange chromatography, affinity chromatography, crystallization, electrofocusing, and preparative gel electrophoresis. Limulus $\alpha_2$-macroglobulin can also be generated recombinantly or synthesized chemically given the sequence disclosed in Iwaki et al. (1996).

Monoclonal antibodies which specifically bind to Limulus $\alpha_2$-macroglobulin specifically bind to epitopes present in Limulus $\alpha_2$-macroglobulin, such as $\alpha_2$-macroglobulin having the amino acid sequence disclosed in Iwaki et al. (1996). Preferably, the $\alpha_2$-macroglobulin epitopes recognized by the monoclonal antibody are not present in other Limulus proteins. Typically, at least 6, 8, 10, or 12 contiguous amino acids are required to form an epitope. However, epitopes which involve non-contiguous amino acids may require more, e.g., at least 15, 25, or 50 amino acids. Monoclonal antibodies which specifically bind to Limulus $\alpha_2$-macroglobulin provide a detection signal at least 5-, 10-, or 20-fold higher than a detection signal provided with other proteins when used in Western blots or other immunochemical assays. Preferably, monoclonal antibodies which specifically bind to Limulus $\alpha_2$-macroglobulin do not detect other proteins in immunochemical assays and can immunoprecipitate Limulus $\alpha_2$-macroglobulin from solution.

Monoclonal antibodies especially useful in the broad practice of the present invention inhibit the enzymatic activation of the lysate, which can be detected by cleavage of chromogenic substrates or the formation of a gel clot, in the presence of endotoxin but not in the presence of glucan when specifically bound to Limulus $\alpha_2$-macroglobulin in a Limulus amebocyte lysate. Chromogenic substrates suitable for use in LAL-endotoxin assays are also suitable for a glucan assay. Any such monoclonal antibody having this preferential impact on lysate reactivity is within the scope of the present invention. In a more preferred embodiment, the monoclonal antibody is monoclonal antibody 7A10. This antibody and three others which specifically bind Limulus $\alpha_2$-macroglobulin were generated in mice using purified Limulus $\alpha_2$-macroglobulin and a ClonaCell™-HY hybridoma cloning kit (StemCell Technologies Inc.). The standard ClonaCell™-HY protocol was followed, except that the pre-fusion medium, Medium A, did not contain gentamicin. These monoclonal antibodies can be used in a method to purify Limulus $\alpha_2$-macroglobulin Hybridoma cells which secrete the monoclonal antibody 7A10 were deposited on Oct. 7, 1997, with the American Type Culture Collection, 10801 University Boulevard, Manassas, Va. 20110-2209, under accession number ATCC HB-12415. This deposit will be maintained under the terms of the Budapest Treaty and is incorporated herein by reference. The content of the deposit is controlling in the event of a discrepancy between the deposit and the written description herein.

Other monoclonal antibodies which specifically bind to an epitope of a Limulus $\alpha_2$-macroglobulin to which a monoclonal antibody 7A10 specifically binds can also be generated using routine hybridoma methodologies. Antibodies which compete with 7A10 for the same epitope on the Limulus $\alpha_2$-macroglobulin can be detected by using the candidate antibodies in competition assays with labeled 7A10 antibodies, a procedure understood by those skilled in the art. 7A10 antibodies can be labeled, for example, with a radioactive or fluorescent tag, and the ability of another monoclonal antibody to compete with the labeled 7A10 antibody for a specific epitope on the Limulus $\alpha_2$-macroglobulin can be detected, for example by fluorescence activated cell sorting, scintillation counting, or other methods, as is known in the art.

The concentration of monoclonal antibody required to achieve maximum inhibition of the amebocyte lysate's response to a specific level or concentration of endotoxin can be determined for each particular antibody, as described in Example 1, below. In a preferred embodiment using the monoclonal antibody 7A10, the concentration of antibody required to achieve complete inhibition (100%) of the lysate's response to endotoxin at a concentration of 0.5 EU/ml was about 6 $\mu$g/ml.

The monoclonal antibodies of the invention can be isolated and purified by any methods known in the art. For example, the monoclonal antibodies can be affinity purified, by passing hybridoma culture medium over a column to which a Limulus $\alpha_2$-macroglobulin bearing the epitope recognized by the antibody is bound. Antibody purification using a column containing immobilized protein G, such as ImmunoPure® Plus (Pierce), is preferred. The bound antibodies can then be eluted from the column, for example, using a buffer with a high salt concentration.

The response of an amebocyte lysate to the addition of a sample containing endotoxin or glucan can be detected as is well known in the art, for example by turbidimetric methods, e.g., by observing gel clot formation or by chromogenic methods. Preparation of amebocyte lysate for such assays is routine, and for use in carrying out the assay method of the present invention, any method for preparing the lysate as are well known in the art can be used. Gram-positive bacterial polysaccharides derived from bacteria such as *Staphylococcus epidermidis, Staphylococcus aureas,* or *Streptococcus hemolyticus,* or synthesized lipid A derivatives such as phosphatidylic acid, phosphatidylglycerol, or phosphatidylethanolamine, can be used to test the response of the amebocyte lysate to endotoxin in the presence of a Limulus $\alpha_2$-macroglobulin-specific monoclonal antibody. Preferably, a range of concentrations of endotoxin, for example, 10 ng/ml, 1 ng/ml, 500 pg/ml, 125 pg/ml, 62.5 pg/ml, 31.25 pg/ml, 15.6 pg/ml, 7.8 pg/ml, and 0.00 pg/ml, is used to assess and assure maximal inhibition of the endotoxin response in the presence of the monoclonal antibody.

Synthetic (1→3)-$\beta$-D-glucans, such as "curdlan" or "packiman," or fungal polysaccharides derived from yeasts such as *Candida albicans, Microsporum canis, Aspergillus fumigatus,* or *Saccharomyces cerevisiae,* can be used to test enzymatic activation of the amebocyte lysate containing a Limulus $\alpha_2$-macroglobulin-specific monoclonal antibody in response to glucan. Again, a range of concentrations of glucan, for example, 10 pg/ml, 5 pg/ml, 2.5 pg/ml, 1.25 pg/ml, and 0.00 pg/ml, is recommended to validate the ability of the monoclonal antibody to inhibit enzymatic activation of the lysate in the presence of endotoxin, but not in the presence of glucan. Enzymatic activation of the lysate can be detected by gel clot formation or by cleavage of a chromogenic substrate such as those disclosed in Iwanaga et al., *Hemostasis* 7: 183–88 (1978) and U.S. Pat. No. 4,510, 241.

Monoclonal antibodies of the invention also can be attached to a solid substrate and used to affinity purify a Limulus $\alpha_2$-macroglobulin from a Limulus amebocyte lysate. The solid substrate can be any solid substrate to which proteins can be attached, including but not limited to, beads (such as glass, latex, sepharose, or cellulose beads), filtration membranes (composed of, for example, nitrocellulose or nylon), the inner surface of tubes (such as glass or plastic tubes), or glass or plastic slides or dishes, such as Petri dishes or 6-, 12-, 24-, 48-, or 96-well plates. The surface of the solid substrate can be coated with a substance such as laminin, polylysine or polyornithine to facilitate attachment of the antibody. Alternatively, the surface of the solid substrate can be derivatized with chemically reactive groups, such as carboxyl, sulfhydryl, or amine groups, as is known in the art, to provide attachment sites for the antibody.

For affinity purification of the Limulus $\alpha_2$-macroglobulin, the antibody-coated solid substrate is contacted with a Limulus amebocyte lysate. The lysate is prepared by methods well known in the art. The step of contacting is carried out under conditions wherein the monoclonal antibody reversibly binds to the $\alpha_2$-macroglobulin in the lysate, for example at 4° C., and over sufficient time to permit specific binding to occur. After binding, the solid substrate is then washed, for example with a low salt buffer solution, to remove non-specifically bound proteins. Following the washing step, the $\alpha_2$-macroglobulin which is reversibly bound to the monoclonal antibody can be released. This release can be achieved, for example, by washing the solid substrate with a buffer containing a single concentration or an increasing concentration gradient of an eluent, for example 0.01–1 M HCl, 0.1–1 M acetic acid, pH 2.0, 0.01 M NH$_4$OH, 0.025 M Na$_2$CO$_3$: 0.5 M NaCl, pH 10 to 11.5, 2–4 M KSCN or NaSCN, 2–4 M MgCl$_2$, 1–6 M guanidine HCl, or 1–6 M urea. The released $\alpha_2$-macroglobulin can be concentrated from the buffer solution by methods known in the art, such as dialysis, pressure filtration through a specific molecular weight cut-off membrane filter, electrophoresis, or lyophilization.

The preparation of $\alpha_2$-macroglobulin thus obtained is substantially free from other proteins of the Limulus amebocyte lysate. Purity of the preparation can be assessed by any method known in the art, such as SDS-polyacrylamide gel electrophoresis. Preferably, the preparation of $\alpha_2$-macroglobulin is at least 80% pure; more preferably, the preparation is 90%, 95%, or 99% pure.

For purification of Limulus $\alpha_2$-macroglobulin, use of the monoclonal antibody 7A10 or another monoclonal antibody which reacts with an epitope of Limulus $\alpha_2$-macroglobulin to which 7A10 specifically binds is preferred. Other monoclonal antibodies of the invention can also be used to purify $\alpha_2$-macroglobulin, either from *Limulus polyphemus* or from other species containing an $\alpha_2$-macroglobulin which is cross-reactive with the particular monoclonal antibody used. Such species include other horseshoe crabs, such as *Tachypleus tridentatus* or *Tachypleus gigas*, other arthropods such as the crayfish *Pacifastacus leniusculus*, and vertebrates, including mammals such as rat, mouse, cow, and human.

The monoclonal antibodies of the invention can be used to provide a reagent and a method for specifically detecting the presence of a glucan in a test sample. The reagent comprises an amebocyte lysate and a monoclonal antibody which specifically binds to an epitope on Limulus $\alpha_2$-macroglobulin and inhibits enzymatic activation of the lysate to form a gel clot in the presence of endotoxin. The amebocyte lysate can be prepared using standard methodologies from amebocytes of horseshoe crabs such as *Limulus polyphemus, Tachypleus tridentatus,* or *Tachypleus gigas.* Limulus amebocyte lysate is preferred. Addition of the monoclonal antibody to the amebocyte lysate inhibits the enzymatic activation of the amebocyte lysate in the presence of an endotoxin, but not in the presence of a glucan. The monoclonal antibody 7A10 is preferred, but other monoclonal antibodies which specifically bind to the same epitope of $\alpha_2$-macroglobulin to which 7A10 specifically binds, or antibodies which bind to other epitopes of $\alpha_2$-macroglobulin and result in inhibition of enzymatic activation of the lysate in response to endotoxin, can be used. Such monoclonal antibodies can be obtained using standard hybridoma generating methods and routine screening, as described above.

The reagent of the invention can be supplied in a kit for the specific detection of a glucan in a test sample. The test sample can be any sample in which it would be useful to determine possible yeast contamination, including water and biological samples, including but not limited to tissue culture medium, blood, and serum. The kit contains an amebocyte lysate, preferably a *Limulus polyphemus* amebocyte lysate, and a monoclonal antibody which binds to a Limulus $\alpha_2$-macroglobulin and inhibits the enzymatic activation of the amebocyte lysate in the presence of an endotoxin, but not in the presence of a glucan. The kit can then be used to detect either endotoxin or, upon the addition of the monoclonal antibody to the lysate, to detect glucan specifically, even in the presence of endotoxin.

The following are provided for exemplification purposes only and are not intended to limit the scope of the invention described in broad terms above.

EXAMPLE 1

This example demonstrates the inhibition of the response of a Limulus amebocyte lysate to endotoxin, but not to glucan, by the presence of monoclonal antibody 7A10.

Monoclonal antibody 7A10 was added to a Limulus amebocyte lysate to final concentrations of 1.560 $\mu$g/ml, 3.125 $\mu$g/ml, and 6.250 $\mu$g/ml. The percent inhibition of the lysate's response to endotoxin was assessed by measuring inhibition of chromogenic substrate cleavage in a control lysate which was free of monoclonal antibody and in the lysate samples having the different monoclonal antibody concentrations. Each lysate sample was challenged with 05. EU/ml of endotoxin.

The response of the lysate samples to this level of an endotoxin was completely inhibited at a 7A10 concentration of 6.250 $\mu$g/ml of monoclonal antibody (FIG. 1). Increasing concentrations of a second monoclonal antibody 2D5, which also specifically binds to an epitope on Limulus $\alpha_2$-macroglobulin, but which recognizes a different epitope than monoclonal antibody 7A10, had no inhibitory effect on enzymatic activation in the presence of this level of this level of endotoxin.

Addition of purified monoclonal antibody 7A10 can be used to inhibit the response of a Limulus amebocyte lysate to endotoxin. As a consequence, monoclonal antibody 7A10 allows the practice of an assay which is specific for the detection of glucan in a test sample.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

We claim:

1. A reagent for specifically detecting a glucan in a test sample, comprising:

an amebocyte lysate; and a monoclonal antibody which binds to a Limulus $\alpha_2$-macroglobulin, wherein addition of the monoclonal antibody to the amebocyte lysate inhibits enzymatic activation of the amebocyte lysate in the presence of an endotoxin but not in the presence of a glucan.

2. The reagent of claim 1 wherein the amebocyte lysate is derived from an amebocyte originating from the group consisting of *Limulus polyphemus, Tachypleus tridentatus,* and *Tachypleus gigas.*

3. The reagent of claim 1 wherein the monoclonal antibody specifically binds to an epitope of a Limulus $\alpha_2$-macroglobulin to which a monoclonal antibody which is secreted by a hybridoma cell with ATCC Accession No. HB-12415 specifically binds.

4. The reagent of claim 1 wherein the monoclonal antibody is a monoclonal antibody which is secreted by a hybridoma cell with ATCC Accession No. HB-12415.

5. A kit for specifically detecting a glucan in a test sample, comprising:

an amebocyte lysate; and a monoclonal antibody which binds to a Limulus $\alpha_2$-macroglobulin, wherein addition of the monoclonal antibody to the amebocyte lysate inhibits enzymatic activation of the amebocyte lysate in the presence of an endotoxin but not in the presence of a glucan.

6. The kit of claim 5 wherein the amebocyte lysate is derived from an amebocyte isolated from the group consisting of *Limulus polyphemus, Tachypleus tridentatus,* and *Tachypleus gigas.*

7. The kit of claim 5 wherein the monoclonal antibody specifically binds to an epitope of a Limulus $\alpha_2$-macroglobulin to which a monoclonal antibody which is secreted by a hybridoma cell with ATCC Accession No. HB-12415 specifically binds.

8. The kit of claim 5 wherein the monoclonal antibody is a monoclonal antibody which is secreted by a hybridoma cell with ATCC Accession No. HB-12415.

* * * * *